United States Patent [19]
Corbin et al.

[11] Patent Number: 5,169,870
[45] Date of Patent: Dec. 8, 1992

[54] RECLAIMING EPSILON-CAPROLACTAM FROM NYLON 6 CARPET

[75] Inventors: Thomas F. Corbin, Asheville; Edward A. Davis, Candler; Jack A. Dellinger, Weaverville, all of N.C.

[73] Assignee: BASF Corporation, Parsippany, N.J.

[21] Appl. No.: 718,720

[22] Filed: Jun. 21, 1991

[51] Int. Cl.$^5$ .................. C08J 11/14; C08J 11/16
[52] U.S. Cl. .................... 521/49.8; 521/40.5
[58] Field of Search .............. 521/49.8, 40.5

[56] References Cited

U.S. PATENT DOCUMENTS

| | | | |
|---|---|---|---|
| 2,343,174 | 2/1944 | Edison et al. | 521/49.8 |
| 3,988,406 | 10/1976 | Nakamura et al. | 264/68 |
| 4,028,159 | 6/1977 | Norris | 521/40.5 |
| 4,051,212 | 9/1977 | Grigat et al. | 521/49.8 |
| 4,107,160 | 8/1978 | Dicoi et al. | 422/260 |
| 4,143,001 | 3/1979 | Raab et al. | 521/48 |
| 4,311,642 | 1/1982 | Crescentini et al. | 521/40.5 |

OTHER PUBLICATIONS

Dmitrieva et al., "Regeneration of $\epsilon$-Caprolactam from Wastes . . . ," Translated from *Khimicheskie Volokna*, 17(4), Jul.-Aug. 1985, pp. 5-12.

L. A. Dmitrieva et al., "Regeneration of $\epsilon$-caprolactam from Wastes in the Manufacture of Polycaproamide Fibres and Yarns", *Fibre Chemistry*, Mar. 1986, pp. 229-241.

*Primary Examiner*—Paul R. Michl
*Assistant Examiner*—Andrew E. C. Merriam

[57] ABSTRACT

A process for the continuous recovery of $\epsilon$-caprolactam provides a carpet made from nylon 6 fibers and having a backing to a separator to prepare scrap containing nylon 6 and waste. The scrap from the separator is fed to a depolymerizing reactor where the scrap is subjected to a depolymerization catalyst, temperatures of at least the melting point of nylon 6 and superheated steam to produce an $\epsilon$-caprolactam containing distillate and more waste. The $\epsilon$-caprolactam in the distillate is separated from other volatiles therein; and purified.

9 Claims, 2 Drawing Sheets 5,169,870

1

RECLAIMING EPSILON-CAPROLACTAM FROM NYLON 6 CARPET

FIELD OF THE INVENTION

The present invention relates to a process for reclaiming ϵ-caprolactam. More particularly, the present invention relates to a process for reclaiming ϵ-caprolactam from nylon 6 carpet.

BACKGROUND OF THE INVENTION

As landfills continue to reach capacity, raw materials are depleted and man recognizes that the earth's resources are limited, more and more materials need to be recycled. Synthetic polymers have long presented problems in recycling due to their often being commingled with other materials and sometimes apparently irreversible polymerization from which useful raw materials cannot be obtained easily.

Certain polyamides, however, are known to be hydrolytically degradable and reusable. Especially, in the case of nylon 6, the monomeric starting materials are reclaimed from waste polymer and used in the manufacture of man-made fibers. The literature reveals procedures for reclaiming such monomers and polymers. L. A. Dmitrieva et al, Regeneration of ϵ-caprolactam from Wastes in the Manufacture of Polycaproamide Fibres and Yarns, *Fibre Chemistry*, March 1986, pp. 229–241, describes methods for reclaiming polycaprolactam (nylon 6) waste.

There are generally two methods for reclaiming nylon 6 waste. The first involves reprocessing the waste nylon 6, for example, via extrusion to form useful articles. This concept is demonstrated in U.S. Pat. No. 4,143,001 to Raab et al.

The second method involves chemical regeneration through depolymerization. Processes for depolymerizing solid polyamide waste are known. For example, U.S. Pat. No. 2,343,174 to Edison et al. shows general hydrolytic degradation using steam. U.S. Pat. No. 3,988,406 to Nakamura et al. shows the recycling of polyamide waste by depolymerization.

Among the polyamides depolymerized for re-use of the monomer is nylon 6. For example, U.S. Pat. No. 4,107,160 to Dicoi et al. describes reclamation of solid nylon 6 waste, accumulated during the processing of nylon 6, low molecular weight oligomers and residual monomer from the polycondensation of caprolactam.

Other polymers are also recycled. An example of a process for continuously degrading various plastics is provided in U.S. Pat. No. 4,051,212 to Grigat et al. Grigat et al. shows a process for continuously hydrolytically degrading plastics. The hydrolyzable material is introduced with water into a screw machine, where it is subjected to a temperature of 100° C. to 300° C. at a pressure of 5 to 100 bars for 2 to 100 minutes.

Although the motivation for reclaiming raw materials from waste polymer or spent polymeric products is well recognized, some products do not readily lend themselves to recycling. Especially, items which are composites of several materials present problems. Along these lines, polymeric materials formed into carpets present an interesting reclamation problem. This is due, in part, to the variety of materials present in traditional carpet and the manner in which they are intimately combined. In traditional carpets, the tufts are often nylon 6, while the backing of a nylon 6 tufted carpet may include jute, polypropylene and latex, among other things. Also, the latex may contain fillers such as calcium carbonate, clay or hydrated aluminum. The chemical and physical nature of these materials is such that reclamation of ϵ-caprolactam from nylon 6 carpets has traditionally been considered too complex, too expensive and cumbersome to be practical.

SUMMARY OF THE INVENTION

Accordingly, the present invention is a process for recovering ϵ-caprolactam from nylon 6 carpet, which is made from nylon 6 fibers and has a backing. The carpet can be provided to a separator to prepare scrap containing nylon 6 and a first waste portion. The scrap from the separator is fed to a depolymerizing reactor where the scrap is subjected to a depolymerization catalyst, temperatures of at least the melting point of nylon 6 and superheated steam to produce an ϵ-caprolactam containing distillate and a second waste portion. The ϵ-caprolactam in the distillate is separated from other volatiles therein and purified after separating.

It is an object of the present invention to provide a process for reclaiming ϵ-caprolactam from nylon 6 carpets. Traditional thought was that polypropylene or jute and especially latex would give impurities which would make purification so difficult or the reclaimed yield so low as to render depolymerization of carpets impractical. Moreover, the $CaCO_3$ usually present in the latex as filler would neutralize an equivalent amount of any acid depolymerization catalyst, such as $H_3PO_4$.

Related objects and advantages will be readily apparent to one ordinarily skilled in the art after considering the following.

DESCRIPTION OF THE PREFERRED EMBODIMENTS

To promote an understanding of the principles of the present invention, descriptions of specific embodiments of the invention follow, and specific language describes the same. It will neverthelesss be understood that no limitation of the scope of the invention is thereby intended, and that such alterations and further modifications, and such further applications of the principles of the invention as discussed are contemplated, as would normally occur to one ordinarily skilled in the art to which the invention pertains.

The present invention surprisingly produces from nylon 6 carpets, ϵ-caprolactam which contains only those impurities derived from nylon 6. Although it is preferred that most of the polypropylene and latex or other non-nylon materials are separated by mechanical means, it is not essential. Where mechanical means are used there is much less by-product from depolymerization and the reclamation of ϵ-caprolactam is easier.

Figure 1:
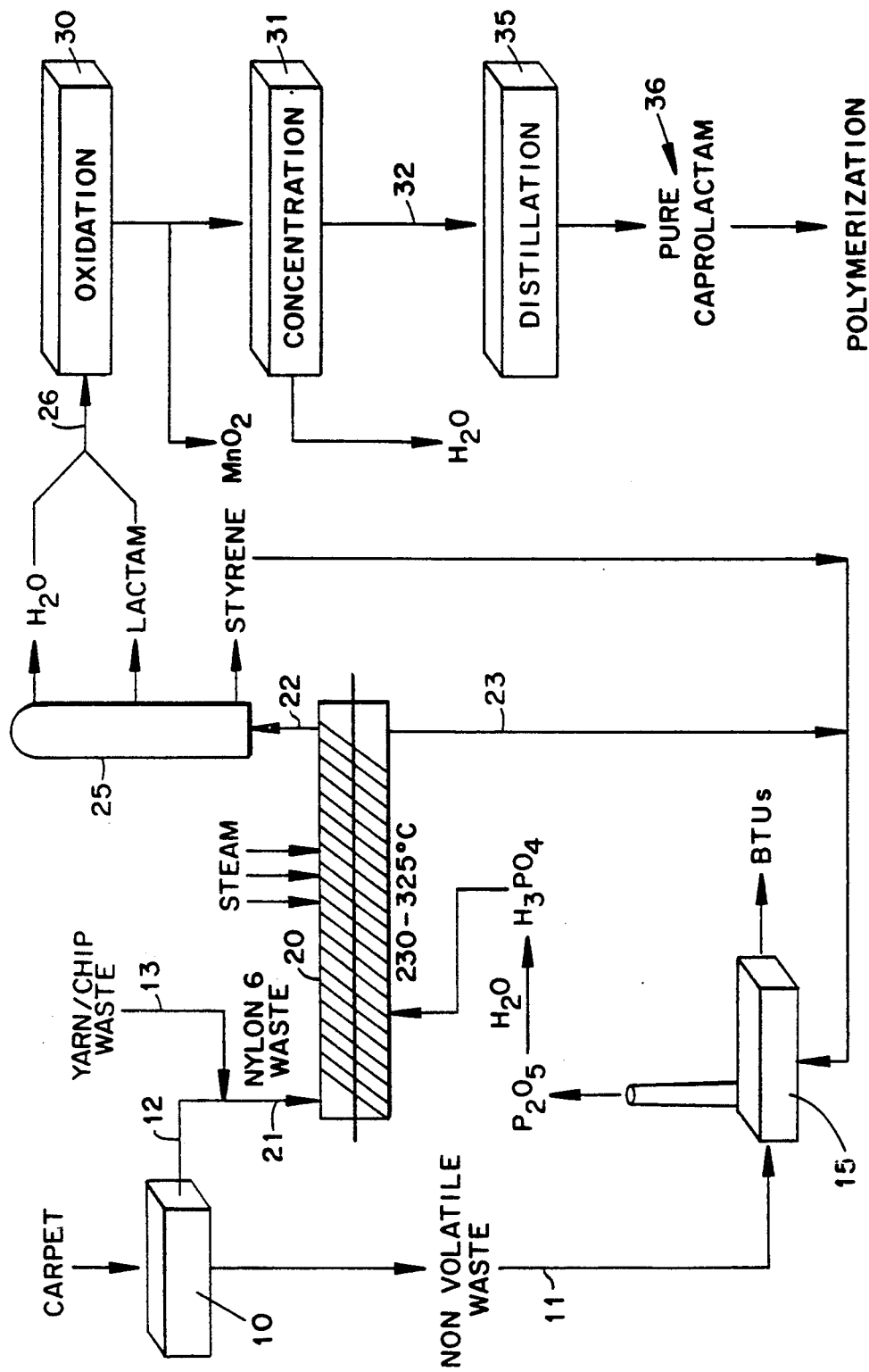
FIG. 1 is a schematic of the process of the present invention.

The process of the present invention is schematically illustrated in FIG. 1. Preferably, in the first step, carpet in strips or pieces is fed to separator 10, in which the carpet is mechanically reduced to a smaller size. A large portion of any non-caprolactam materials, including latex, jute and polypropylene may be removed in the separator by shredding, tearing, grinding, or other mechanical action. Non-volatile waste 11 removed in separator 10 is separated from the nylon 6. Waste 11 is routed away and may, optionally, be directed to power house 15. At power house 15, the waste is used to produce energy. Several separator components suitable for use in the present invention are available from Schirp Corporation as Type 75, Type 38CIII, Type 58, Type 38CII, Type 66, Type 71, Type 66-L, Type 57, Type 57S500, Type 64, and Type 62C.

Figure 2:
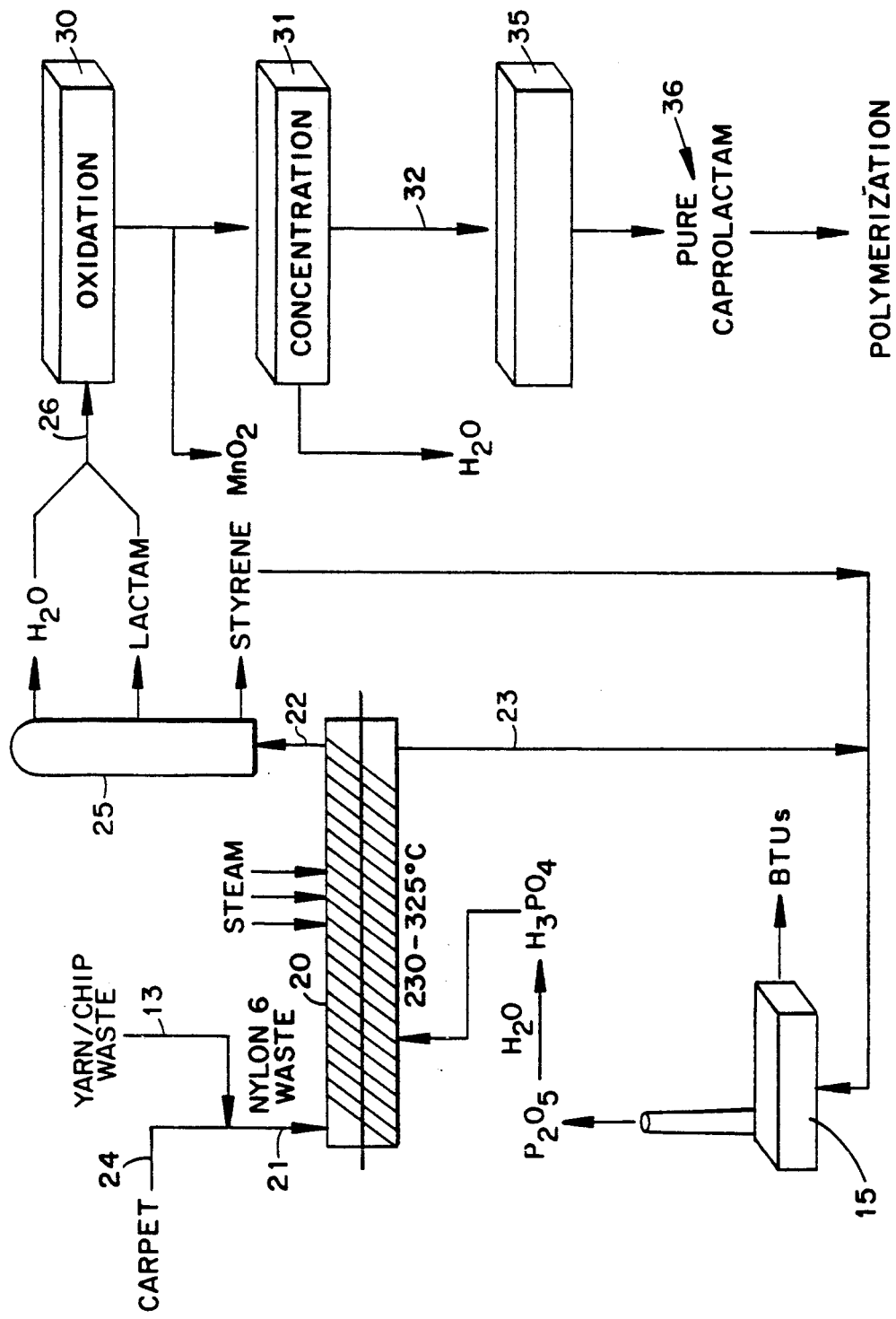
FIG. 2 is a schematic of an alternate process of the present invention.

Nylon 6 (12) obtained from separator 10 is then fed to a continuous depolymerization reactor (CDR) unit 20. A thin film evaporator can be used for depolymerization. Luwa Corporation is one source for such evaporators. It is also possible to feed carpet directly to the CDR, bypassing the separator step. This is shown in FIG. 2 where carpet 24 is fed directly to unit 20, optionally after combination with solid waste 13. The rest of the process is substantially as shown in FIG. 1 so that the reference numbers are the same.

The following description of depolymerization relates to a CDR. However, the continuous depolymerization reactor depolymerization process can be carried out with a batch reactor or other suitable non-continuous reactor. The continuous reactor is preferred mostly because the process does not have to be interrupted to remove nonvolatile reactor bottoms.

Optionally, other nylon 6 solid waste (13), such as yarn waste, chip waste or extruder slag, can be combined with the nylon 6 feed from separator 10 or with the carpet if the separator is not used. Also, optionally, contaminated monomeric caprolactam or caprolactam oligomers, such as from nylon 6 wash water, can be fed to depolymerization unit 20. If a thin film evaporator is used as the CDR, then preferably the waste carpet material is molten prior to feeding into the thin film evaporator. Total waste feed 21 is fed through depolymerization unit 20. One preferred manner of feeding waste 21 is by means of an auger internal to CDR unit 20, but other means for feeding the waste, such as a conveyor belt or gravity feed, should be readily apparent.

In CDR unit 20, a depolymerization catalyst is injected. Preferably, the catalyst is injected downstream from where waste 21 is fed into depolymerization unit 20. One suitable depolymerization catalyst is phosphoric acid, which is preferably provided at a rate to make the acid concentration in the reactor from 1%-10%, more preferably from 5%-7%. Phosphoric acid can be recovered via the reactor waste. Other depolymerization catalysts can also be used, such as boric acid and phosphate salts.

Superheated steam, preferably between about 100° to about 250° C., is provided to CDR unit 20. Preferably, the steam is provided further downstream than the depolymerization catalyst to help distill lactam volatiles as they are formed. It may be added at a rate to give a condensate of up to about 20% lactam in the distillate. But more or less steam can be added depending on the amount of auxiliary heat added to the CDR by other means, e.g. electrical resistance heat to the wall of the CDR.

The depolymerization reactor is preferably maintained at a temperature between about 230° C. and about 325° C., more preferably between about 250° C. to 280° C. The superheated steam volatilizes caprolactam and other volatile compounds out of the melt as these compounds are formed to produce distillate 22.

Distillate 22 is then passed through fractionating column 25, where water and caprolactam are fractionated from other non-aqueous volatile substances, for example, styrene. Nonvolatile residue 23 from CDR unit 20 may, optionally, be routed to power house 15 as a further fuel supply. Styrene produced from fractionating styrene and other non-aqueous volatile distillates from water and aqueous distillates such as ε-caprolactam from the aqueous lactam are optionally routed to power house 15 for fuel. Styrene may optionally be collected for purification and reused. Also, the residue from depolymerization will contain a high concentration of phosphoric acid when phosphoric acid is used as the reaction catalyst. The combustion from residue 23 in power house 15 could allow recovery of the phosphoric acid for reuse.

After fractionation, aqueous lactam-containing stream 26 is subjected to oxidizing agent 30 to oxidize residual impurities which were not removed by the fractionation column to compounds which can be more easily separated in the subsequent process steps. Oxidizing agent 30 is preferably potassium permanganate, preferably provided at about 25° to about 75°, preferably at about 40° C., but other oxidizing agents are also useful. For example, $H_2O_2$, $K_2Cr_2O_7$, sodium or potassium hypochlorites, perchlorites, and perboric acid are useful. When the oxidizing agent is potassium permanganate, it is preferably supplied at about 1-5 wt. % of the caprolactam but more may be used depending on how impure the lactam may be. For example, more potassium permanganate is required for more impure lactam. Manganese dioxide may be filtered out as a by-product of the oxidative treatment.

The oxidized aqueous caprolactam is then concentrated when subjected to concentration step 31. Concentration is preferably accomplished by evaporation at elevated temperature of the water, optionally under reduced pressure.

After concentration, concentrated ε-caprolactam stream 32 is fed to a vacuum distillation unit for additional purification. The distillation preferably takes place at about 100° C. to about 150° C. under a reduced pressure of less than about 20 mm Hg using a thin film evaporator. Epsilon-caprolactam 36 suitable for fiber production is provided after vacuum distillation. Epsilon-caprolactam 36 is useful for all common uses of ε-caprolactam, including repolymerization to form nylon carpet fiber.

The invention will be described by referring to the following detailed examples. These examples are set forth by way of illustration and are not intended to be limiting in scope.

EXAMPLE 1

108 grams of nylon carpet backed with polypropylene and latex are fed to a Schirp separator. Much of the backing material is removed and passed to the feed of a power generator. The nylon portion is charged to a film evaporator with 30.0 mL of 85% phosphoric acid. Superheated steam is injected continuously during the 45 minute reaction. The vapor temperature in the evaporator is 250° C.–300° C. The distillate collected (1040 mL) contains about 2.9% ε-caprolactam (as determined by GC) and thus given a crude yield of about 56%.

The solids from the reactor are passed to the feed of a power generator. The emissions of the generator upon burning the solids contains $P_2O_5$, which is reacted with water to regenerate phosphoric acid.

The distillate is passed through a fractionating column where non-aqueous volatiles are removed and routed to the power generator. The fractionated aqueous phase is treated with 1-2% KMnO$_4$ at about 40°-50° C. Water is removed by evaporation to concentrate the oxidized aqueous phase. After vacuum distillation, nearly pure ε-caprolactam is obtained which is suitable for blending with virgin lactam and repolymerization.

EXAMPLE 2

The procedure of Example 1 is followed except that the Schirp separator is bypassed. The carpet containing nylon 6 is charged directly, after heating, to the thin film evaporator. Nearly pure ε-caprolactam is obtained which is suitable for reuse in making nylon 6.

EXAMPLE 3

108 grams of nylon 6 carpet, backed with CaCO$_3$ filled latex and polypropylene, is charged to a 1000 ml three-neck round bottom flask with 6 ml of 85% phosphoric acid. Superheated steam is injected continuously during the 45-minute reaction. The vapor temperature of the reaction is 250° C. -300° C. A distillate of 1065 ml is condensed and collected. The distillate contains 1.9% ε-caprolactam. A small quantity of non-aqueous phase is separated from the distillate. The remaining aqueous phase is treated with 2% KMnO$_4$ at 40° C.-50° C. for 2 hours. The water is removed by evaporation to produce solid ε-caprolactam. The solid ε-caprolactam is distilled under about 1 mm Hg to yield pure ε-caprolactam.

what is claimed is:

1. A process for the recovery of ε-caprolactam from nylon 6 carpet, comprising:
   a) providing a carpet made from nylon 6 fibers and having a non-nylon 6 backing containing one or more non-nylon 6 materials of polypropylene, jute, latex and fillers to a mechanical separator to prepare scrap containing both nylon 6 and non-nylon 6 backing materials, and a first waste portion;
   b) feeding the scrap from the separator to a depolymerizing reactor where the scrap is subjected to a depolymerization catalyst, temperatures of at least the melting point of nylon 6 and superheated steam to produce an ε-caprolactam containing distillate and a second waste portion;
   c) separating ε-caprolactam in the distillate from other volatiles therein; and
   d) purifying the ε-caprolactam obtained after separating so that the ε-caprolactam is of sufficient purity for reuse as a starting material for nylon 6 intended for use in carpet fiber.

2. The process of claim 1 further comprising e) routing the first and second waste portions to a power generating means as fuel for power production.

3. The process of claim 1 wherein said separating is by fractional distillation to obtain an aqueous fraction and a non-aqueous fraction.

4. The process of claim 3 further comprising h) sending the non-aqueous fraction to a power generating means.

5. The process of claim 1 wherein said purifying is by oxidizing the aqueous fraction, concentrating the oxidized aqueous fraction and distilling the concentrated oxidized aqueous fraction.

6. The process of claim 1 wherein said feeding is carried out continuously.

7. A process for recovering ε-caprolactam from nylon 6 carpet comprising:
   a) providing a carpet made from nylon 6 fibers and having a backing containing one or more non-nylon 6 materials of polypropylene, jute, latex and fillers to a mechanical separator to prepare scrap containing both nylon 6 and non-nylon 6 backing materials, and a first waste portion;
   b) feeding the scrap from the separator to a depolymerizing reactor where the scrap is subjected to a depolymerization catalyst, temperatures of at least the melting point of nylon 6 and superheated steam to produce an ε-caprolactam containing distillate and a second waste portion;
   c) separating ε-caprolactam in the distillate from other volatiles therein; and
   d) purifying the ε-caprolactam obtained after separating so that the purified ε-caprolactam is suitable for use as a starting material for nylon 6 carpet fiber;
   e) routing the first and second waste portions to a power generating means as fuel for power production; and
   f) sending the non-aqueous volatiles to the power generating means.

8. A process for reclaiming ε-caprolactam from nylon 6 carpet comprising:
   a) providing a carpet tufted with nylon 6 and having a backing containing latex for recycling;
   b) feeding the carpet to a depolymerization reactor;
   c) subjecting the carpet in the depolymerization reactor to a depolymerization catalyst present at about 1% to about 10% of the carpet weight at a temperature of about 230° C. and 325° C. to produce volatile monomers and a first waste portion;
   d) separating the volatile monomers from the first waste portion; and
   e) fractionating the volatile monomers to yield ε-caprolactam and a second waste portion.

9. The process of claim 8 further comprising using the first and second waste portions as feed for a power generating means.

* * * * *